US008318687B2

(12) United States Patent
Tabira et al.

(10) Patent No.: US 8,318,687 B2
(45) Date of Patent: Nov. 27, 2012

(54) RECOMBINANT ADENO-ASSOCIATED VIRUS VECTOR FOR TREATMENT OF ALZHEIMER DISEASE

(75) Inventors: Takeshi Tabira, Obu (JP); Hideo Hara, Obu (JP)

(73) Assignees: Takeshi Tabira, Tokyo (JP); Hideo Hara, Fukuoka (JP)

( * ) Notice: Subject to any disclaimer, the term of this patent is extended or adjusted under 35 U.S.C. 154(b) by 658 days.

(21) Appl. No.: 10/560,280

(22) PCT Filed: Jun. 11, 2004

(86) PCT No.: PCT/JP2004/008224
§ 371 (c)(1),
(2), (4) Date: Apr. 26, 2006

(87) PCT Pub. No.: WO2004/111250
PCT Pub. Date: Dec. 23, 2004

(65) Prior Publication Data
US 2009/0004144 A1    Jan. 1, 2009

(30) Foreign Application Priority Data

Jun. 13, 2003  (JP) ................................. 2003-169714
Oct. 30, 2003  (JP) ................................. 2003-371103

(51) Int. Cl.
*A61K 48/00*  (2006.01)
*A61K 39/00*  (2006.01)
*A61K 39/38*  (2006.01)
*C07H 21/02*  (2006.01)
*C07H 21/04*  (2006.01)

(52) U.S. Cl. .................. 514/44 R; 424/184.1; 536/23.1

(58) Field of Classification Search ................ 514/44 R; 424/184.1; 536/23.1
See application file for complete search history.

(56) References Cited

U.S. PATENT DOCUMENTS

| | | | | |
|---|---|---|---|---|
| 5,854,204 A | * | 12/1998 | Findeis et al. ................... | 514/2 |
| 2003/0165481 A1 | * | 9/2003 | Hersh ........................ | 424/93.21 |
| 2005/0255113 A1 | * | 11/2005 | Huston et al. .............. | 424/145.1 |

FOREIGN PATENT DOCUMENTS

| | | | |
|---|---|---|---|
| WO | WO 99/27944 A1 | | 6/1999 |
| WO | WO 00/39310 A1 | | 7/2000 |
| WO | WO 00/72880 A2 | | 12/2000 |
| WO | WO 02/36614 | * | 5/2002 |
| WO | WO 02/096350 A2 | | 12/2002 |
| WO | WO 2004/050876 A1 | | 6/2004 |

OTHER PUBLICATIONS

Askanas Transfer of beta-amyloid precursor protein gene using adenovirus vector causes mitochondrial abnormalities in cultured normal human muscle. Proc Natl Acad Sci U S A. 93(3):1314-9, 1996.*
Kuwako et al.,Activation of calpain in cultured neurons overexpressing Alzheimer amyloid precursor protein, Brain Res Mol Brain Res. 107(2):166-75, 2002.*
Wyss-Coray et al., TGF-beta1 promotes microglial amyloid-beta clearance and reduces plaque burden in transgenic mice, Nat. Med. 7(5):612-8, 2001.*
Patricia A. Gonnella et al., "In Situ Immune Response in Gut-Associated Lymphoid Tissue (GALT) Following Oral Antigen in TCR-Transgenic Mice", The Journal of Immunology, 1998, pp. 4708-4718.
James A.R. Nicoll et al., "Neuropathology of human Alzheimer disease after immunization with amyloid-β peptide: a case report", Nature Medicine, Apr. 2003, pp. 448-452, vol. 9, No. 4.
Tony Wyss-Coray et al., "Chronic Overproduction of Transforming Growth Factor-β1 by Astrocytes Promotes Alzheimer's Disease-Like Microvascular Degeneration in Transgenic Mice", American Journal of Pathology, Jan. 2000, pp. 139-150, vol. 156, No. 1.
R.J. Bland et al., "Generation of Rat Alzheimers Disease Models Utilizing Adeno-Associated Virus to Target Transgenes to the Hippocampus", Soceity for Neuroscience Abstract Viewer and Itinerary Planner, 2002, vol. 2002, pp. Abstract, No. 295.12.
Martin Citron et al., "Mutation of the B-amyloid precursor protein in familiar Alzheimer's disease increases B-protein production", Nature, Dec. 17, 1992, pp. 672-674, vol. 360.
Jie Kang et al., "The precursor of Alzheimer's disease amyloid A4 protein resembles a cell-surface receptor", Nature, Feb. 19, 1987, pp. 733-736, vol. 325.
P.A. Lewis et al., "Expression of Bri-amyloid B peptide fusion proteins: a novel method for specific high-level expression of amyloid B peptides", Biochimica et Biophysica Acta, 2001, pp. 58-62, vol. 1537.
Shang Zhen Zhou et al., "Adeno-associated Virus 2-mediated High Efficiency Gene Transfer into Immature and Mature Subsets of Hematopoietic Progenitor Cells in Human Umbilical Cord Blood", J. Exp. Med., 1994, pp. 1867-1875, vol. 179.
E.M. Johnstone et al., "Nuclear and Cytoplasmic Localization of the B-Amyloid Peptide (1-43) in Transfected 293 Cells", Biochemical and Biophysical Research Communications, 1996, pp. 710-718, vol. 220, Article. No. 0469.
Matthew J. During et al., "An Oral Vaccine Against NMDAR1 with Efficacy in Experimental Stroke and Epilepsy", Science, Feb. 25, 2000, pp. 1453-1460, vol. 287.
Elisabeth Tarkowski et al., "Increased intrathecal levels of the angiogenic factors VEGF and TGF-B in Alzheimer's disease and vascular dementia", Neurobiology of Aging, 2002, pp. 237-243, vol. 23.

* cited by examiner

*Primary Examiner* — Wu-Cheng Winston Shen
(74) *Attorney, Agent, or Firm* — Wenderoth, Lind & Ponack, L.L.P.

(57) ABSTRACT

Disclosed is an adeno-associated virus vector capable of expressing a peptide fragment containing a humoral immunity induction site of the β-amyloid peptide, comprising DNA encoding the peptide fragment in an operative form.

14 Claims, 5 Drawing Sheets

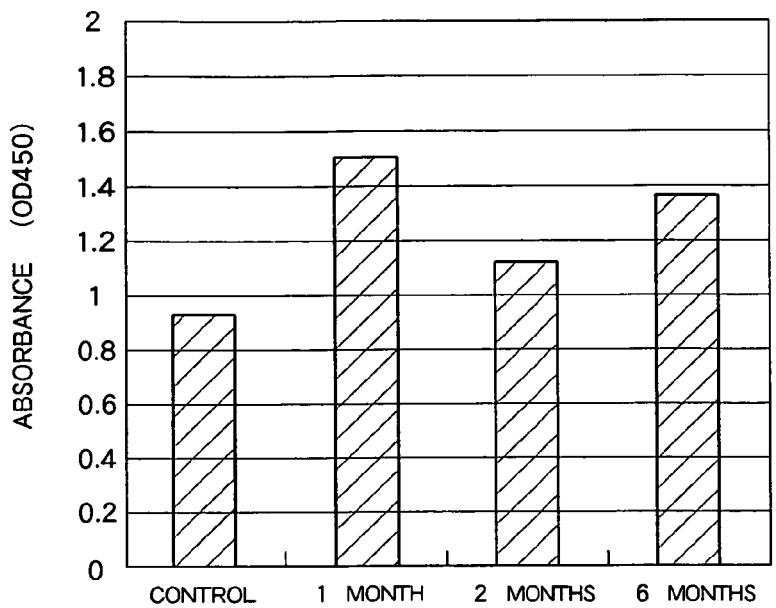
F I G. 1
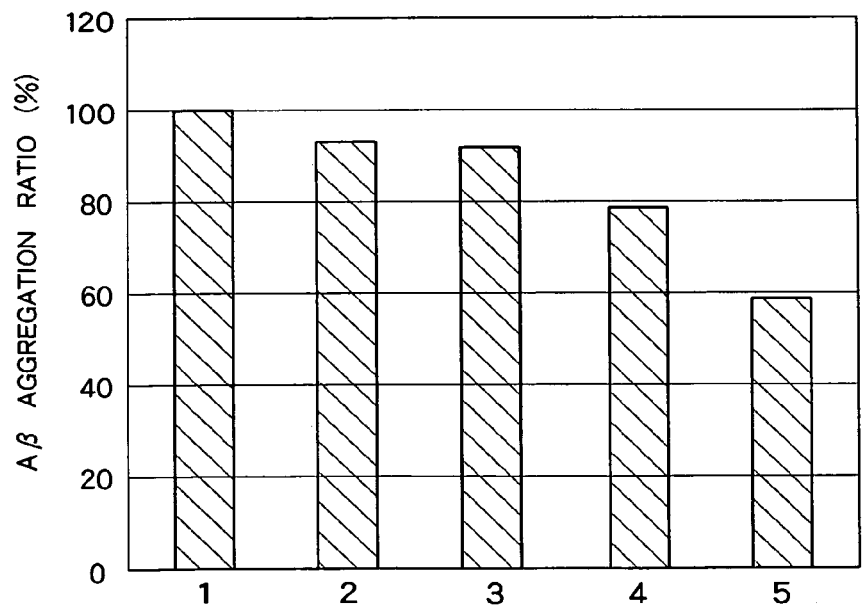
F I G. 2

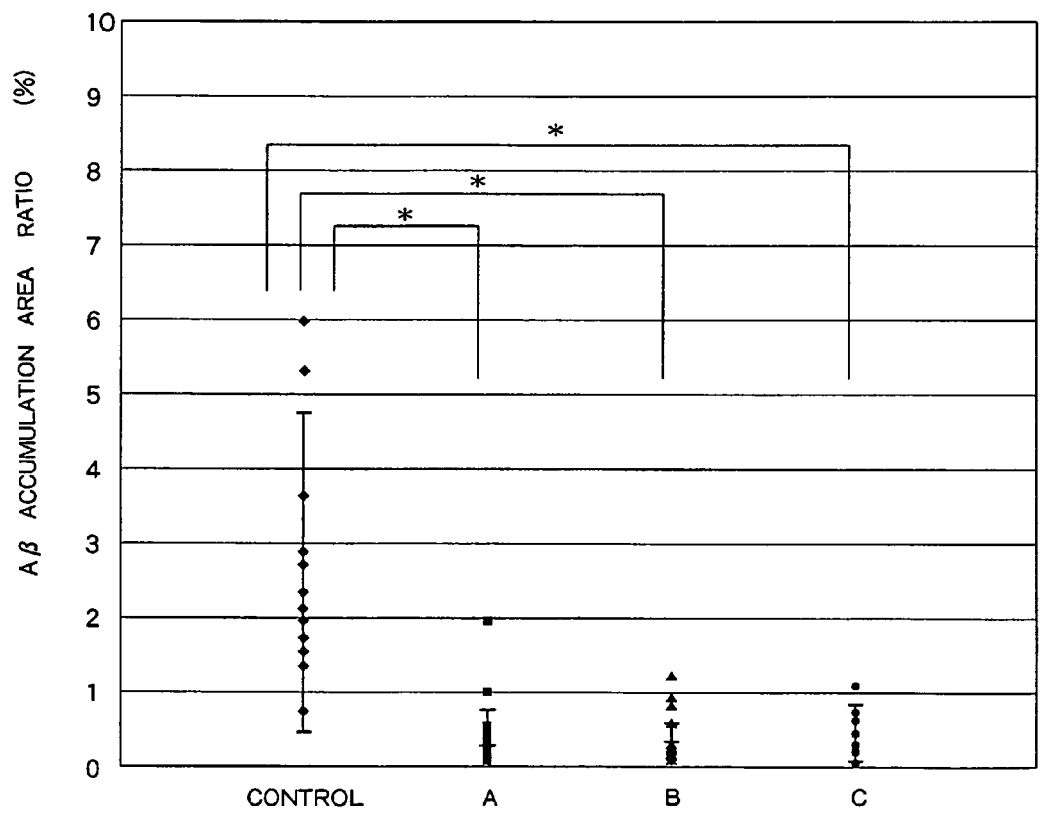
F I G. 4

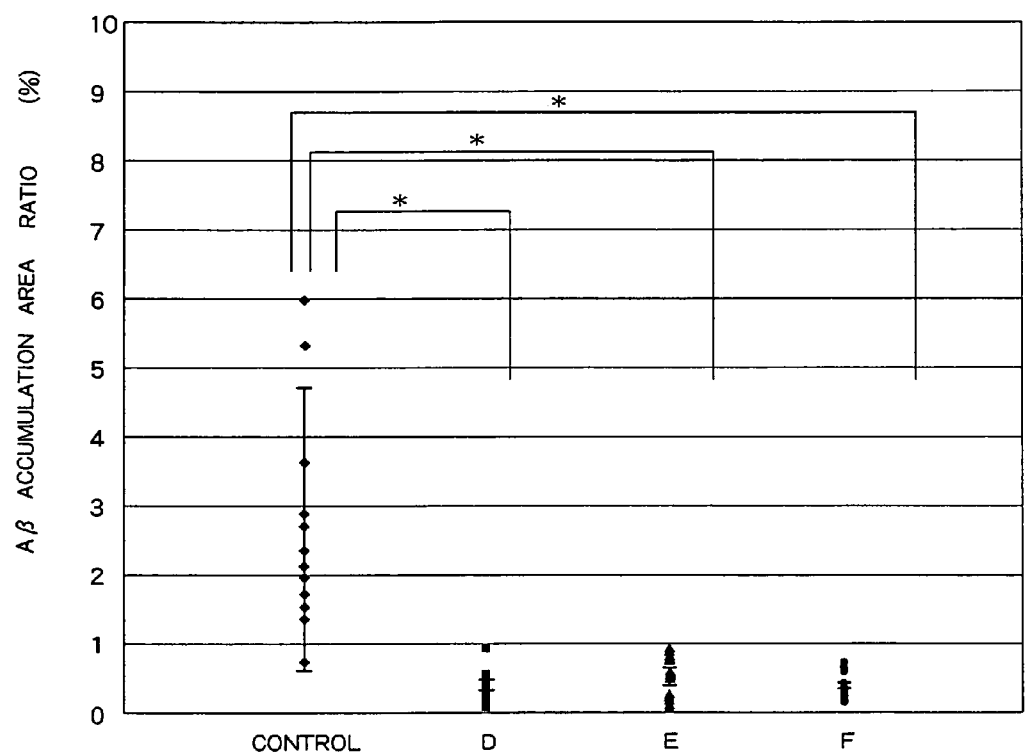
F I G. 5

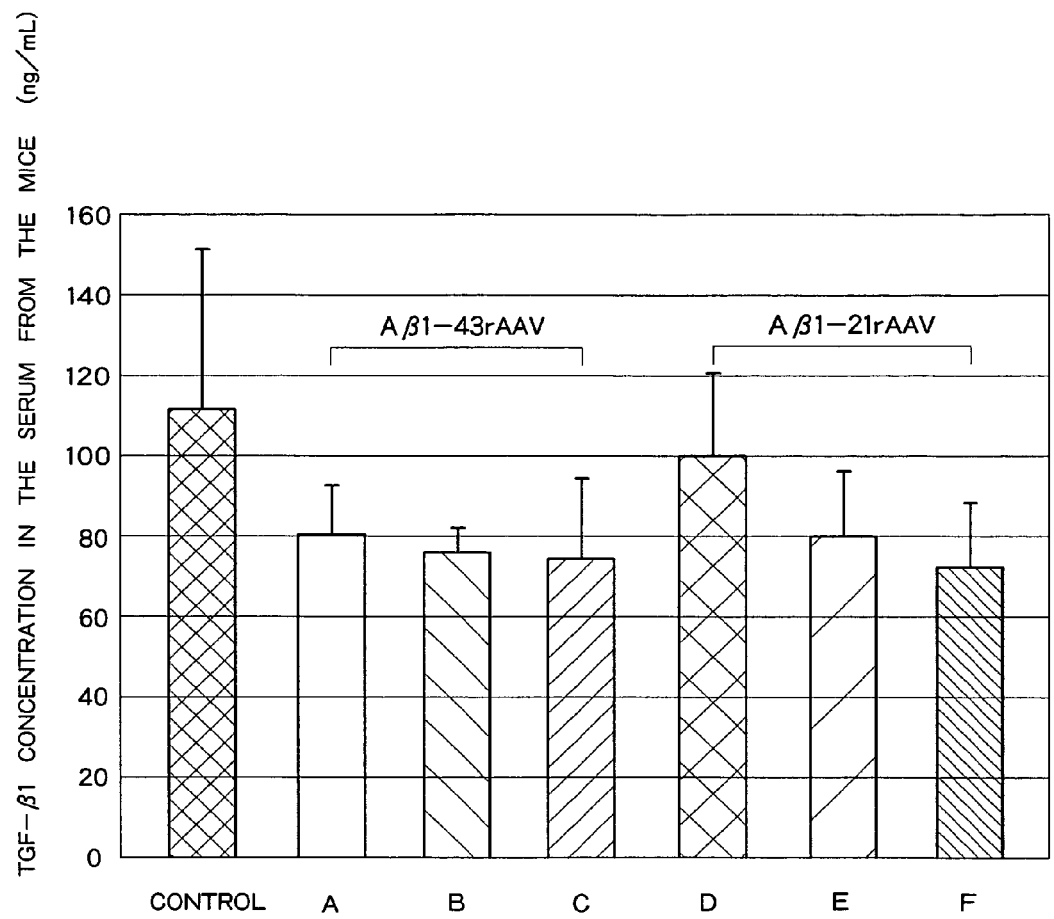
F I G. 6

SEQUENCE LISTING

```
<160> NUMBER OF SEQ ID NOS: 19

<210> SEQ ID NO 1
<211> LENGTH: 129
<212> TYPE: DNA
<213> ORGANISM: Homo sapiens
<220> FEATURE:
<221> NAME/KEY: CDS
<222> LOCATION: (1)..(129)

<400> SEQUENCE: 1 gat gca gaa ttc cga cat gac tca gga tat gaa gtt cat cat caa aaa         48
Asp Ala Glu Phe Arg His Asp Ser Gly Tyr Glu Val His His Gln Lys
  1               5                  10                  15 ttg gtg ttc ttt gca gaa gat gtg ggt tca aac aaa ggt gca atc att         96
Leu Val Phe Phe Ala Glu Asp Val Gly Ser Asn Lys Gly Ala Ile Ile
```

-continued

```
                    20                  25                  30
gga ctc atg gtg ggc ggt gtt gtc ata gcg aca                         129
Gly Leu Met Val Gly Gly Val Val Ile Ala Thr
            35                  40
```

<210> SEQ ID NO 2
<211> LENGTH: 43
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40

<210> SEQ ID NO 3
<211> LENGTH: 63
<212> TYPE: DNA
<213> ORGANISM: Homo sapiens
<220> FEATURE:
<221> NAME/KEY: CDS
<222> LOCATION: (1)..(63)

<400> SEQUENCE: 3

```
gat gca gaa ttc cga cat gac tca gga tat gaa gtt cat cat caa aaa   48
Asp Ala Glu Phe Arg His Asp Ser Gly Tyr Glu Val His His Gln Lys
1               5                   10                  15 ttg gtg ttc ttt gca                                                 63
Leu Val Phe Phe Ala
            20
```

<210> SEQ ID NO 4
<211> LENGTH: 21
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15

Leu Val Phe Phe Ala
            20

<210> SEQ ID NO 5
<211> LENGTH: 54
<212> TYPE: DNA
<213> ORGANISM: Homo sapiens
<220> FEATURE:
<221> NAME/KEY: CDS
<222> LOCATION: (1)..(54)

<400> SEQUENCE: 5

```
atg ctg ccc ggt ttg gca ctg ctc ctg ctg gcc gcc tgg acg gct cgg   48
Met Leu Pro Gly Leu Ala Leu Leu Leu Leu Ala Ala Trp Thr Ala Arg
1               5                   10                  15 gcg ctt                                                             54
Ala Leu
```

<210> SEQ ID NO 6
<211> LENGTH: 18
<212> TYPE: PRT
<213> ORGANISM: Homo sapiens

-continued

```
<400> SEQUENCE: 6

Met Leu Pro Gly Leu Ala Leu Leu Leu Ala Ala Trp Thr Ala Arg
1               5                   10                  15

Ala Leu

<210> SEQ ID NO 7
<211> LENGTH: 197
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (9)..(191)

<400> SEQUENCE: 7 ggtctaga atg ctg ccc ggt ttg gca ctg ctc ctg ctg gcc gcc tgg acg      50
         Met Leu Pro Gly Leu Ala Leu Leu Leu Ala Ala Trp Thr
         1               5                   10 gct cgg gcg ctt gat gca gaa ttc cga cat gac tca gga tat gaa gtt       98
Ala Arg Ala Leu Asp Ala Glu Phe Arg His Asp Ser Gly Tyr Glu Val
15              20                  25                  30 cat cat caa aaa ttg gtg ttc ttt gca gaa gat gtg ggt tca aac aaa       146
His His Gln Lys Leu Val Phe Phe Ala Glu Asp Val Gly Ser Asn Lys
                35                  40                  45 ggt gca atc att gga ctc atg gtg ggc ggt gtt gtc ata gcg act           191
Gly Ala Ile Ile Gly Leu Met Val Gly Gly Val Val Ile Ala Thr
            50                  55                  60 taagac                                                                197

<210> SEQ ID NO 8
<211> LENGTH: 61
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Met Leu Pro Gly Leu Ala Leu Leu Leu Ala Ala Trp Thr Ala Arg
1               5                   10                  15

Ala Leu Asp Ala Glu Phe Arg His Asp Ser Gly Tyr Glu Val His His
            20                  25                  30

Gln Lys Leu Val Phe Phe Ala Glu Asp Val Gly Ser Asn Lys Gly Ala
        35                  40                  45

Ile Ile Gly Leu Met Val Gly Gly Val Val Ile Ala Thr
    50                  55                  60

<210> SEQ ID NO 9
<211> LENGTH: 137
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (17)..(133)

<400> SEQUENCE: 9
tggcggccgc tctaga atg ctg ccc ggt ttg gca ctg ctc ctg ctg gcc gcc    52
               Met Leu Pro Gly Leu Ala Leu Leu Leu Ala Ala
               1               5                   10
```

-continued

```
tgg acg gct cgg gcg ctt gat gca gaa ttc cga cat gac tca gga tat      100
Trp Thr Ala Arg Ala Leu Asp Ala Glu Phe Arg His Asp Ser Gly Tyr
        15                  20                  25 gaa gtt cat cat caa aaa ttg gtg ttc ttt gct taag                      137
Glu Val His His Gln Lys Leu Val Phe Phe Ala
    30                  35
```

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

```
Met Leu Pro Gly Leu Ala Leu Leu Leu Ala Ala Trp Thr Ala Arg
 1               5                  10                  15

Ala Leu Asp Ala Glu Phe Arg His Asp Ser Gly Tyr Glu Val His His
                20                  25                  30

Gln Lys Leu Val Phe Phe Ala
                35
```

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatgcagaat tccgacatga ctcagga                                          27

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtcttaagtc gctatgacaa caccgccc                                         28

<210> SEQ ID NO 13
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggtctagaat gctgcccggt ttggcactgc tcctgctggc cgcctggacg gctcgggcgc      60
tt                                                                    62

<210> SEQ ID NO 14
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
```

```
agcgcccgag ccgtccaggc ggccagcagg agcagtgcca aaccgggcag cattctagac    60
c                                                                    61

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtctagaat gctgcccggt ttggcac                                        27

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggcggccgc tctagaatg                                                 19

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cacatcttaa gcaaagaaca cc                                             22

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agtgaaccgt cagatcgc                                                  18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cggtatcagc tcactcaa                                                  18
```

RECOMBINANT ADENO-ASSOCIATED VIRUS VECTOR FOR TREATMENT OF ALZHEIMER DISEASE

This application is a national stage of PCT/JP2004/008224 filed Jun. 11, 2004. The entire contents of the above-identified application is hereby incorporated by reference.

BACKGROUND OF THE INVENTION

1. Field of the Invention

The present invention relates to an adeno-associated virus vector expressing Aβ peptide, which can be used for the treatment of Alzheimer's disease, and its use as a pharmaceutical agent.

2. Background Art

Alzheimer's disease is characterized by senile (neuritic) plaques, neurofibrillary tangles, and the alteration and depletion of neural cells in the brain. In particular, β-amyloid deposited in senile plaques is considered to play a central role in pathological development of Alzheimer's disease. β-Amyloid peptide (Aβ), the major component of this β-amyloid deposit, is produced by partial decomposition of β-amyloid precursor protein (βAPP) by β- and γ-secretases in neural cells.

Recently, it is disclosed that the formation of senile plaques was suppressed and the number of existing senile plaques was reduced by administering Aβ peptide along with an adjuvant for immunization to transgenic mice which have familial forms of Alzheimer pathology and overexpress a human amyloid precursor protein (Schenk D., Barbour R., Dunn W. et al.: Nature 400:173-177, 1999).

As putative mechanisms for the abovementioned reactions, three theories are now proposed. According to the first theory, the antibody against Aβ produced in the body by Aβ peptide administration binds the aggregated Aβ in senile plaques and microglial phagocytosis of the resulting product elicits the clearance of the senile plaques. The antibody also binds secreted Aβ and microglial phagocytosis of the resulting product elicits the suppression of cytotoxicity of Aβ to neural cells. These lead to the treatment of dementia and the like. According to the second theory, the antibody against AD produced by Aβ peptide administration binds Aβ by recognizing its N terminus amino acid to solubilize aggregated or insolubilized Aβ and further to suppress aggregation and deposition of secreted Aβ, which results in the reduction in amyloid deposition. According to the third theory, so-called "sink" theory, the antibody against Aβ does not pass through the blood-brain barrier but it diffuses Aβ from the central nerve system to the peripheral system by reducing Aβ in the peripheral blood and peripheral tissue.

Based on the abovementioned theories, development of preventive and therapeutic methods for Alzheimer's disease has also been attempted with virus vectors. For example, it is described that oral administration of an adenovirus vector, in which Aβ cDNA is incorporated, to C57BL/6 mice enabled Aβ to be expressed in the tissues of the upper gastrointestinal tract in the mice and that the anti-Aβ antibody in the mouse serum inhibited the aggregation of Aβ peptide in vitro (Takeshi Tabira and Hideo Hara, Fiscal 2002 Welfare Science Research, "21 Century-Type Medical Pioneering/Promoting Research (Field of Dementia), Publication Report on Research Results" published by Incorporated Foundation, Japan Foundation for Longevity Science (Choju Kagaku Shinko Zaidan), March 2002, pp. 49-54). In this report, however, no in vivo experiment has been reported and therapeutic effect in animals has not been confirmed.

Furthermore, it is known that the cytokine TGF-β1 (transforming growth factor β1) promotes the production of inflammatory cytokines (IL-1β (interleukin-1β), TNF-α (tumor necrosis factor-α and the like) in vascular endothelial cells. Further, recently, it was reported that TGF-β1 promoted Alzheimer's disease-related pathological changes such as cerebrovascular amyloid deposition and microvascular degeneration (Wyss-Coray, T. et al.: Amyloidogenic role of cytokine TGF-β1 in transgenic mice and Alzheimer's disease: Nature 389: 603-606, 1997 and Wyss-Coray, T. et al.: Chronic overproduction of transforming growth factor-β1 by astrocytes promotes Alzheimer's disease-like microvascular degeneration in transgenic mice: Am. J. Pathol. 156: 139-150, 2000).

Therapeutic agents for Alzheimer's disease have to suppress senile plaque formation and amyloid deposition in the central nervous system and at the same time should not diffuse into other organs or cause side effects such as encephalitis for safety. However, no therapeutic agent to meet these requirements utilizing the Aβ antigen has so far been reported.

SUMMARY OF THE INVENTION

We have now found that amyloid deposition and senile plaque formation is reduced in the brain by expressing in intestinal cells Aβ antigen inducing humoral immunity, thereby inducing the production of the antibody against this Aβ antigen, using a recombinant adeno-associated virus (rAAV). Further, we have also found that no inflammatory observation is found in the brain and other organs such as kidneys when this recombinant adeno-associated virus is used. The present invention is based on these findings.

Accordingly, an object of the present invention is to provide an adeno-associated virus vector expressing Aβ antigen and a pharmaceutical composition comprising the vector, which can be used for treatment of Alzheimer's disease.

The adeno-associated virus vector according to the present invention is an adeno-associated virus vector capable of expressing a peptide fragment containing a humoral immunity induction site of β-amyloid peptide and comprises DNA encoding this peptide fragment in an operative form.

Further, the pharmaceutical composition for the treatment of Alzheimer's disease according to the present invention comprises the adeno-associated virus vector of the present invention.

According to the present invention, with the use of the recombinant adeno-associated virus vector, antibody production can be induced without inducing cellular immune responses and senile plaque formation and amyloid deposition in the central nerve system can be suppressed. Further, with the use of this recombinant adeno-associated virus, the concentration of TGF-β1 in the blood can be reduced and the progress of cerebrovascular amyloid deposition and cerebral microvascular degeneration can be suppressed. Further, according to the recombinant adeno-associated virus vector of the present invention, a highly safe treatment for Alzheimer's disease is possible without causing side effects such as encephalitis and liver disorder.

BRIEF DESCRIPTION OF THE DRAWINGS

FIG. 1 shows the amount of anti-Aβ antibody production in the serum from the mice to which the adeno-associated virus vector expressing Aβ1-43 was orally administered.

FIG. 2 shows the suppressive effect of anti-Aβ antibody in the mouse serum on Aβ aggregation in vitro.

FIG. 4 shows the average Aβ accumulation area ratios in frontal lobe cortex, parietal lobe and hippocampus regions in the mice to which the adeno-associated virus vector expressing Aβ1-43 was orally administered.

FIG. 5 shows the average Aβ accumulation area ratios in frontal lobe cortex, parietal lobe and hippocampus regions in the mice to which the adeno-associated virus vector expressing Aβ1-21 was orally administered.

FIG. 6 shows the TGF-β1 concentration in the serum from the mice to which the adeno-associated virus vector expressing Aβ1-43 or Aβ1-21 was orally administered.

DETAILED DESCRIPTION OF THE INVENTION

Figure 3:
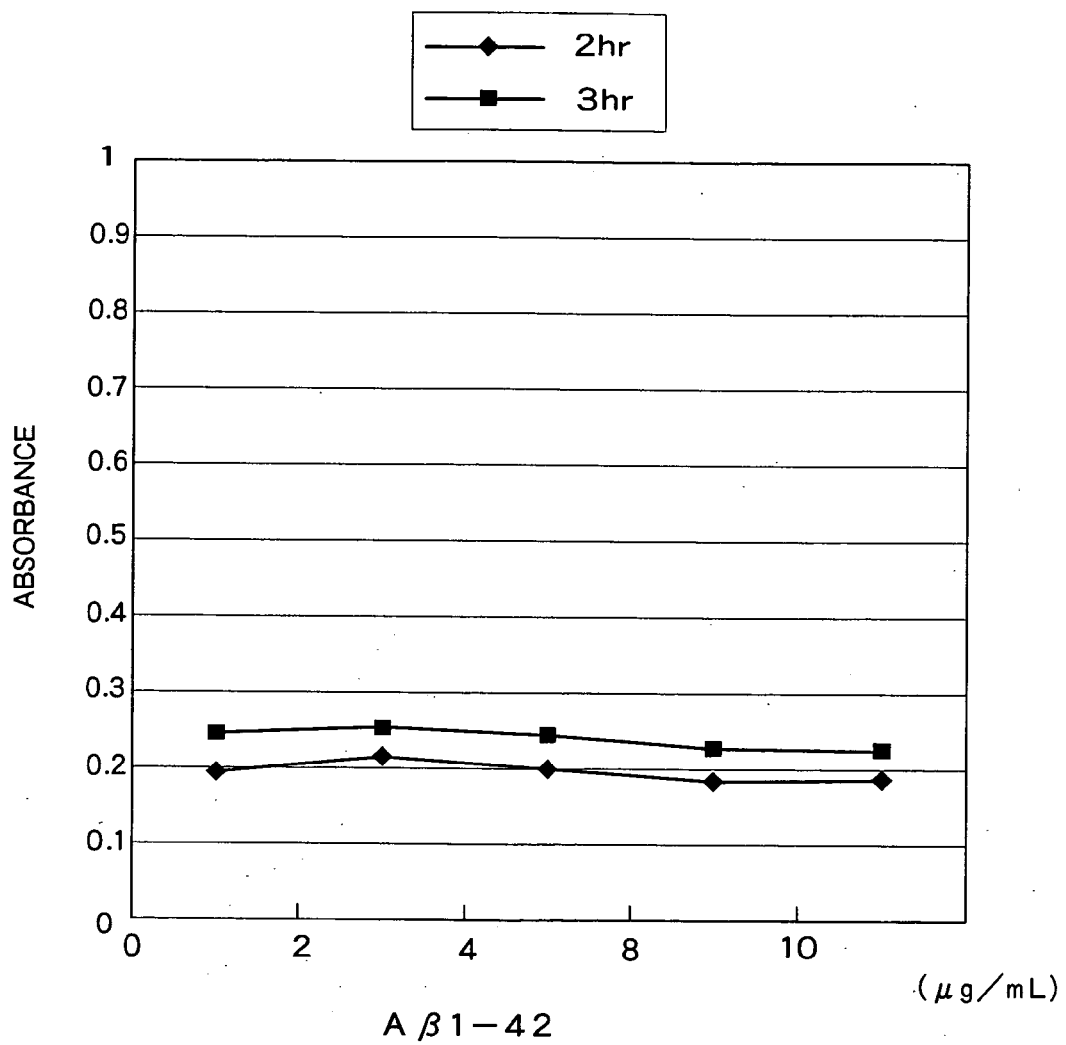
FIG. 3 shows the cell proliferation reactivity of spleen cells of the treated mice to Aβ42 peptide.

An adeno-associated virus vector according to the present invention comprises a DNA encoding a peptide fragment containing a humoral immunity induction site of β-amyloid peptide (Aβ peptide) in an operative form, thereby said peptide fragment can be expressed. The expression "in an operative form" used herein means that the transferred gene (DNA) is inserted into the vector in a mode in which said gene can be expressed under the control of appropriate regulatory elements (i.e., promoters, enhancers, and transcription terminators).

The humoral immunity induction site of Aβ peptide can be easily specified by anyone skilled in the art. For example, the above-mentioned humoral immunity induction site is present in the region of amino acid residues 4 to 10 of Aβ peptide (Aβ4-10). Accordingly, the abovementioned antigen peptide fragment to be expressed by the adeno-associated virus vector of the present invention preferably comprises Aβ4-10.

Further, an example of the amino acid sequence of Aβ4-10 is amino acids 4 to 10 in the amino acid sequence as shown in SEQ ID NO: 2. Accordingly, the abovementioned antigen peptide fragment preferably comprises amino acids 4 to 10 in the amino acid sequence as shown in SEQ ID NO: 2. The nucleotide sequence of DNA encoding this amino acid sequence is not particularly limited; for example, the nucleotides 10 to 30 in the nucleotide sequence as shown in SEQ ID NO: 1 can be used. Accordingly, the DNA encoding the abovementioned antigen peptide fragment preferably comprises the nucleotides 10 to 30 in the nucleotide sequence as shown in SEQ ID NO: 1.

According to a preferred embodiment of the present invention, the abovementioned antigen peptide fragment comprises amino acids 1 to 43 of Aβ peptide (Aβ1-43). An example of the amino acid sequence of Aβ1-43 is the amino acid sequence as shown in SEQ ID NO: 2; accordingly, the abovementioned antigen peptide fragment preferably comprises the amino acid sequence as shown in SEQ ID NO: 2. The nucleotide sequence of DNA encoding this amino acid sequence is not particularly limited; for example, the nucleotide sequence as shown in SEQ ID NO: 1 can be used. Accordingly, the DNA encoding the abovementioned antigen peptide fragment preferably comprises the nucleotide sequence as shown in SEQ ID NO: 1.

According to another preferred embodiment of the present invention, the abovementioned antigen peptide fragment comprises amino acids 1 to 21 of Aβ peptide (Aβ1-21). An example of the amino acid sequence of Aβ1-21 is the amino acid sequence as shown in SEQ ID NO 4; accordingly, the abovementioned antigen peptide fragment preferably comprises the amino acid sequence as shown in SEQ ID NO: 4. The nucleotide sequence of DNA encoding this amino acid sequence is not particularly limited; for example, the nucleotide sequence as shown in SEQ ID NO: 3 can be used. Accordingly, the DNA encoding the abovementioned antigen peptide fragment preferably comprises the nucleotide sequence as shown in SEQ ID NO: 3.

The abovementioned amino acid sequences of Aβ1-43 and Aβ-21 contain not only a humoral immunity induction site but also a T-cell receptor recognition sequence; however, these antigen peptide fragments primarily induce antibody production and hardly induce cellular immune responses when expressed in the intestinal mucosal immune system by the adeno-associated virus vector of the present invention.

In order to effectively present the abovementioned antigen peptide fragment expressed by the adeno-associated virus vector of the present invention as an antigen, said antigen peptide fragment is preferably secreted outside the infected cells after being expressed inside the cells. Accordingly, the adeno-associated virus vector according to the present invention preferably comprises a DNA encoding a signal peptide enabling the abovementioned expressed antigen peptide fragment to be extracellularly secreted, in an operative form. The expression "to comprise in an operative form" as used herein means that the abovementioned signal peptide is expressed together with the abovementioned antigen peptide fragment and at the same time the expressed said antigen peptide fragment is secreted extracellularly by said signal peptide. The method for integrating the DNA encoding the abovementioned signal peptide into the adeno-associated virus vector of the present invention in an operative form can be any method known to those skilled in the art; for example, a fusion gene in which the two DNAs are so fused that said signal peptide is expressed with its N terminus attached to said antigen peptide fragment.

The abovementioned signal peptide can be any known to those skilled in the art; however, the signal peptide located in the N terminus of amyloid precursor protein (APP) is preferably used. An example of the amino acid sequence of the APP signal peptide is the amino acid sequence as shown in SEQ ID NO: 6; accordingly, the above-mentioned signal peptide to be expressed by the adeno-associated virus vector of the present invention preferably comprises the amino acid sequence as shown in SEQ ID NO: 6. The nucleotide sequence of DNA encoding this amino acid sequence is not particularly limited; for example, the sequence as shown in SEQ ID NO: 5 can be used. Accordingly, the DNA encoding the abovementioned signal peptide preferably comprises the nucleotide sequence as shown in SEQ ID NO: 5.

According to a preferred embodiment of the present invention, the adeno-associated virus vector of the present invention comprises DNA encoding a fused protein in which the APP signal peptide is attached to the N terminus of Aβ1-43. An example of the amino acid sequence of this fused protein is the amino acid sequence as shown in SEQ ID NO: 8 and an example of the nucleotide sequence of DNA encoding this is nucleotides 9 to 191 in the nucleotide sequence as shown in SEQ ID NO: 7.

According to another preferred embodiment of the present invention, the adeno-associated virus vector of the present invention comprises DNA encoding a fused protein in which the APP signal peptide is attached to the N terminus of Aβ1-21. An example of the amino acid sequence of this fused protein is the amino acid sequence as shown in SEQ ID NO: 10 and an example of the nucleotide sequence of DNA encoding this is nucleotides 17 to 133 in the nucleotide sequence as shown in SEQ ID NO: 9.

Further, the adeno-associated virus vector according to the present invention may contain regulatory elements, such as promoters, enhancers and transcription terminators, to effectively express the target DNA and, if necessary, translation start codons and translation stop codons may be inserted therein.

The adeno-associated virus vector according to the present invention can be prepared by a standard method known in the art. For example, U.S. Pat. No. 5,858,351 and the references cited therein describe various recombinant adeno-associated viruses suitable for use in gene therapy and methods for constructing and multiplying these vectors (for example, Kotin (1994) Human Gene Therapy 5:793-801 or Berns "Parvoviridae and their Replication" Fundamental Virology, the second edition compiled by Fields & Knipe).

According to a preferred method for constructing an adeno-associated virus vector, first, ITRs on both ends of the wild-type adeno-associated virus are left and a gene of interest is inserted between them to construct a plasmid (AAV vector plasmid). On the other hand, a plasmid expressing the Rep gene (a gene encoding the replication initiation protein) and the Cap gene (a gene encoding a virus capsid protein) and a plasmid expressing adenovirus genes E2A, E4 and VA are prepared. Next, these three kinds of plasmids are co-transfected into packaging cells expressing the E1 gene, such as HEK293 cells, and the resulting cells are then cultured. In this way, adeno-associated virus vector particles having high infectivity to mammalian cells can be produced. This method can easily be carried out using a commercially available kit such as AAV-Helper-Free System (Stratagene).

The adeno-associated virus vector according to the present invention can be used for treating Alzheimer's disease in mammals. Accordingly, according to the present invention, there is provided a method of treating Alzheimer's disease comprising administering the adeno-associated virus vector of the present invention in a therapeutically effective amount to subjects and use of the adeno-associated virus vector of the present invention in manufacturing therapeutic agents for Alzheimer's disease. The term "therapy" as used herein refers not only to the therapy of established pathological conditions but also to the prevention of pathological conditions to possibly be established in future. The abovementioned subjects can be mammals such as rodents, canines, cats, cattle, and primates, preferably humans.

A method for administering the adeno-associated virus vector according to the present invention can be a method usable in the field of gene therapy, such as intraperitoneal injection, intratracheal injection, intrabronchial injection and direct intrabronchial instillation, subcutaneous injection, transcutaneous administration, intra-arterial infusion, and intravenous injection (see Flotte and Carter, Gene Therapy 2:357-362 (1995)). Further, adeno-associated viruses can be advantageously administered orally since they are not easily attacked by gastric juice. Further, oral administration is particularly preferable because subjects can perform the administration by themselves.

The amount of the adeno-associated virus vector to be administered can be any therapeutically effective amount and such amount can be easily determined by those skilled in the art of gene therapy. Further, the dosage is preferably adjusted according to the severity of pathological conditions, sex, age, body weight and habit of the subject, and the like; however, such dosage is appropriately adjusted by a physician or veterinarian. For example, the amount of the adeno-associated virus vector for oral administration is normally $0.5 \times 10^{11}$ to $2.0 \times 10^{12}$ viral genome/kg of body weight, preferably $1.0 \times 10$ to $1.0 \times 10^{12}$ viral genome/kg of body weight, more preferably $1.0 \times 10^{11}$ to $5.0 \times 10^{11}$ viral genome/kg of body weight. The adeno-associated virus vector according to the present invention is pharmaceutically safe within the range of the abovementioned dosages. The unit "viral genome" as used herein represents the number of adeno-associated virus genome molecules (number of viral particles) and is known to those skilled in the art to represent the amount of adeno-associated virus vectors. The value can be determined by diluting a purified adeno-associated virus solution to carry out dot blot hybridization and comparing its signal intensity with that of plasmid DNA having a specified number of molecules.

The adeno-associated virus vector according to the present invention maintains its therapeutic activity against Alzheimer's disease over a relatively long period of time once administered to a subject. In particular, when orally administered in the abovementioned amount, the antigen is presented in intestinal epithelial cells for at least 6 months and induction of the production of the antibody directed to this antigen has been confirmed. In the light of these findings, anyone skilled in the art can plan an appropriate dosage schedule.

The adeno-associated virus vector according to the present invention can be administered to a subject as a pharmaceutical composition containing it. Accordingly, according to the present invention, there is provided a pharmaceutical composition for the treatment of Alzheimer's disease comprising the adeno-associated virus vector of the present invention. According to a preferred embodiment of the present invention, this pharmaceutical composition is for oral administration.

The pharmaceutical composition according to the present invention can be produced by a method known in the art depending on its administration route and dosage form. For example, dosage forms such as capsules and solutions can be used for a pharmaceutical composition for oral administration. Accordingly, the pharmaceutical composition according to the present invention can contain pharmaceutically acceptable carriers, diluting agents, preservatives, and the like, depending on individual dosage forms.

EXAMPLES

The present invention is further illustrated in detail by the following examples that are not intended to limit the scope of the invention. The mice used in the following test examples are APP transgenic mice, a mouse model of Alzheimer's disease (Tg2576, Taconic, Mayo Clinic).

Example 1

Construction of Adeno-Associated Virus Vector Expressing APP Signal Sequence+Aβ1-43 cDNA Amyloid-β1-43 (Aβ1-43) cDNA was amplified by PCR using the human amyloid precursor protein (APP) gene as a template and the following primers. The PCR reaction solution contained TAPS buffer (25 mM, pH 9.3), KCl (50 mM), $MgCl_2$ (2 mM), 2-mercaptoethanol (1 mM), dNTPs (100 µM), template DNA (50-100 ng), and primers (0.2 µM each). The PCR thermal reaction was performed for 30 cycles, each cycle consisting of 30 seconds at 94° C., 1 minute at 68° C., and 3 minutes at 72° C.

Primers

```
Forward:
5'-GATGCAGAATTCCGACATGACTCAGGA-3,'
and
                                        (SEQ ID NO: 11)
Reverse:
5'-GTCTTAAGTCGCTATGACAACACCGCCC-3'
having an AflII site at the 3' end)
                                        (SEQ ID NO: 12
```

The adaptor for APP secretion signal, first signal sequence at the N terminus (SEQ ID NO: 10), was constructed by treating the following two oligonucleotides for 3 minutes at 90° C. followed by annealing at room temperature.

Oligonucleotides

Sense:
(SEQ ID NO: 13)
5'-GGTCTAGAATGCTGCCCGGTTTGGCACTGCTCCTGCTGGCCGCCTGG

ACGGCTCGGGCGCTT-3'

Antisense:
(SEQ ID NO: 14)
5'-AGCGCCCGAGCCGTCCAGGCGGCCAGCAGGAGCAGTGCCAAACCGGG

CAGCATTCTAGACC-3'

The APP secretion signal adaptor (having a overhanging T residue at the 3' end of the sense chain) and the PCR-amplified Aβ1-43 cDNA (having a overhanging A residue at the 3' end of the antisense chain) were joined together and PCR was performed using the resulting DNA as a template and the following primers to construct a fusion gene, APP signal sequence+Aβ1-43 cDNA (SEQ ID NO: 7 having an XbaI recognition site at nucleotides 3 to 8 in this sequence), in which the APP signal sequence is attached to the 5' end of the Aβ1-43 cDNA. The PCR reaction solution contained TAPS buffer (25 mM, pH 9.3), KCl (50 mM), $MgCl_2$ (2 mM), 2-mercaptoethanol (1 mM), dNTPs (100 μM), template DNA (50-100 ng), and primers (0.2 μM each). The PCR thermal reaction was performed for 30 cycles, each cycle consisting of 30 seconds at 94° C., 1 minute at 68° C., and 3 minutes at 72° C.

Primers

Forward: 5'-GGTCTAGAATGCTGCCCGGTTTGGCAC-3'
(SEQ ID NO: 15 having an XbaI site at the 5' end)

Reverse: 5'-GTCTTAAGTCGCTATGACAACACCGCCC-3'
(SEQ ID NO: 12 having an AflII site at the 5' end)

Since DNA having an appropriate length (4-4.5 kbp) is required to effectively obtain DNA packaging of the adeno-associated virus, the PvuII-SalI fragment of pBR322 plasmid DNA was attached to the APP signal sequence+Aβ1-43 cDNA (XbaI-AflII/blunt) as an unfunctional "stuffer" DNA and then ligated into the standard adeno-associated virus vector (pXXUF1) at the XbaI-SalI site.

Further, in the same manner as in Example 1, three kinds of vectors, i.e., the abovementioned recombinant pXXUF1, a standard Rep/Cap plasmid and the E2A/E4/VA plasmid were gene-transfected into HEK293 cells by the calcium phosphate method and the resulting HEK293 cells were cultured in a large volume, after which virus particles were purified from the cell lysate by CsCl ultracentrifugation to obtain the adeno-associated virus vector having APP signal sequence+Aβ1-43 cDNA.

Example 2

Construction of Adeno-Associated Virus Vector Expressing APP Signal Sequence+Aβ1-21 cDNA APP signal sequence+Aβ1-43 cDNA (XbaI-AflII/blunt) was ligated into the pBluescript plasmid (XbaI-SmaI). PCR was performed using this as a template and the following primers.

Primers

Forward:
5'-TGGCGGCCGCTCTAGAATG-3'     (SEQ ID NO: 16, having a NotI site at the 5' end)

Reverse:
5'-CACATCTTAAGCAAAGAACACC-3'  (SEQ ID NO: 17)

PCR products of the APP signal sequence+Aβ1-21 cDNA (SEQ ID NO: 9 having a NotI restriction site at nucleotides 3-10 and an XbaI restriction site at nucleotides 11-16 in this sequence) were subjected to the NotI-AflII/blunt treatment and the resulting products were ligated into pXXUF1 (NotI-SalI) together with the abovementioned "stuffer" pBR322 PvuII-SalI fragment.

Further, in the same manner as in Example 1, the adeno-associated virus vector having the APP signal sequence+Aβ1-21 cDNA was obtained.

Comparative Example 1

As a control, an adeno-associated virus (GFPrAAV) expressing GFP (green fluorescent protein) was constructed.

Test 1
Western Blot Assay

The APP signal sequence+Aβ1-43 cDNA was ligated into the expression vector pXXUF1 and the resulting product was transfected into HEK293 cells using lipofectamine 2000 (Invitrogen) for 48 hours, after which the culture supernatant and cell lysate were extracted and individually subjected to immunoprecipitation with the anti-Aβ antibody (4G8) and then SDS-PAGE electrophoresis. Next, proteins were transferred to a nitrocellulose membrane and then the detection of Aβ protein was attempted using the anti-Aβ antibody. As a result, it was confirmed that Aβ is extracellularly secreted forming oligomers and that a large amount of 4-kDa Aβ peptide monomer protein was produced inside the cells.

Test 2
Sampling of Mouse Serum

The adeno-associated virus vector of Example 1 ($5 \times 10^{11}$ viral genome) was orally administered only once to a mouse at 15 weeks of age. Serum samples were taken from this mouse 1 month, 4 months, and 6 months after the administration.

Detection of Anti-Aβ Antibody in Mouse Serum

Aβ1-42 peptide (5 mg/ml) was coated onto each well of a 96-well plate (Nunc, MaxiSorp) and blocked with 5% non-fat milk/TBS-T buffer, after which the abovementioned sampled mouse serum (at 500-fold dilution) was added and the detection was performed with a peroxidase-labeled anti-mouse IgG antibody. The antibody titer was evaluated by measuring the optical absorbance with an ELISA reader. The results are shown in FIG. 1.

The antibody titer in the serum primarily reached a peak level one month after the oral administration and continuous antibody production was observed up to 6 months.

Test 3
Test for Inhibition of Aβ Aggregation Reaction by Mouse Serum

The concentration of Aβ1-40 peptide was adjusted to 120 mM and incubation was performed at 37° C. After 24 hours, the start of Aβ aggregation was observed. The mouse serum was added to this Aβ aggregate at ratios of 1:10 and 1:20 (vol:vol) and incubation was performed at 37° C. for one week. Whether the mouse serum inhibited the bonding/aggregation of Aβ1-40 was measured by adding 2 mM thioflavin-T and using a spectrofluorescence meter (excitation at 445 nm; emission at 490 nm). The results are shown in FIG. 2.

The mouse serum sampled 6 months after the administration of the adeno-associated virus vector as in Test Example 1 significantly inhibited aggregation/bonding of Aβ1-40 in vitro as compared to the control mouse serum.

Test 4
DNA Extraction from Tissues and PCR

The heart, lung, spleen, liver, upper gastrointestinal tract, and kidney were extracted from a mouse 28 weeks after oral administration of the adeno-associated virus vector of Example 1 and each tissue was homogenized in a Tris solution, after which the homogenates were subjected to proteolysis with proteinase K and phenol/chloroform treatment to purify DNA. Next, the following primers were constructed from a 5' end nucleotide sequence of the promoter region of the adeno-associated virus vector (pXXUF1) and a 3' end nucleotide sequence of the vector to perform PCR. The PCR reaction solution contained TAPS buffer (25 mM, pH 9.3), KCl (50 mM), $MgCl_2$ (2 mM), 2-mercaptoethanol (1 mM), dNTPs (100 μM), template DNA (50-100 ng), and primers (0.2 μM each). The thermal reaction was performed for 30 cycles, each cycle consisting of 1 minute at 94° C., 0.20 seconds at 68° C., and 1 minute at 72° C. The PCR products were subjected to electrophoresis on 2% agarose gel and stained with ethidium bromide.

Primers

```
Forward: 5'-AGTGAACCGTCAGATCGC-3'    (SEQ ID NO: 18)

Reverse: 5'-CGGTATCAGCTCACTCAA-3'    (SEQ ID NO: 19)
```

The 500 bp band representing the PCR product of interest was recognized only with the tissue from the upper gastrointestinal tract.

Test 5
Cell Proliferation Response of Mouse Spleen Cells to Aβ1-42 Peptide

Spleen cells were isolated from a mouse 28 weeks after oral administration of adeno-associated virus vector of Example 1 and placed onto a 96-well plate ($5 \times 10^4$ cells per well) and incubated for 48 hours in culture solutions with Aβ1-42 peptide added at various concentrations. After completion of the cell culture, a tetrazolium salt (WST-1) was added. Since the tetrazolium salt is transformed into a formazan dye by mitochondrial succinate-tetrazolium reductase that is active only in viable cells, cell proliferation response was assessed by measuring the optical absorbance of the dye solution using an ELISA reader. The results are shown in FIG. 3.

The spleen cells of the mouse given oral administration of the adeno-associated virus vector of the Example 1 showed a low cell proliferation response independently of the Aβ1-42 peptide concentration.

Test 6
Tissue Staining Test 1

Tissue samples were obtained from mice given oral administration of the adeno-associated virus of Example 1 (hereinafter referred to as "treatment group") and from untreated age-matched mice (hereinafter referred to as "control group") 6 months after the administration (at 10 months of age) and the following experiment was carried out using frozen sections of the tissue. In order to detect Aβ protein, senile plaques and the like in the tissue, the tissue was treated with 70% formic acid and endogenous peroxidase was inactivated with 5% $H_2O_2$. After reacting with anti-Aβ antibody (4G8, at 1000-fold dilution) or rabbit anti-Aβ40 antibody (at 1000-fold dilution), peroxidase-labeled second antibody was added and DAB staining was performed.

In the control group, amyloid deposition was developed with age; the deposition was slightly observed in the brain at 6 months of age, while the amyloid deposition became prominent, the senile plaque formation was also recognized, and the amyloid deposition in neural cells was also observed occasionally at 10 months of age.

On the other hand, in the treatment group, expression of Aβ protein was recognized in the epithelial cells of upper gastrointestinal tract upon dissection 6 months after administration (at 10 months of age). Brain dissection 6 months after administration showed that amyloid deposition was apparently reduced and senile plaques were drastically reduced as compared to the control group. The result of the counting of amyloid plaques in the sagittal section of the brain 6 months after administration is shown in Table 1.

TABLE 1

Comparison of brain amyloid deposition in mice in control group and treatment group

| Group | Extracellular amyloid plaques | Intracellular amyloid plaques |
| --- | --- | --- |
| Control group | 76 | ++ |
| Treatment group | 8 | ± |

Mice: at 10 months of age

The average number of amyloid plaques was 76 in the control group, whereas it was 8 in the treated group being reduced by about 90%. The amyloid deposition inside the neural cells occasionally observed in the control group was hardly recognized in the treatment group.

Test 7
Tissue Staining Test 2

In the same manner as in Test Example 6, tissue samples were obtained from the treatment group and the control group 6 months after administration (at 10 months of age) and the following experiment was performed using frozen sections of the tissue. The frozen sections were stained using antibodies such as anti-CD4 antibody, anti-CD86 antibody, anti-CD11b antibody, anti-GFAP antibody (astrocyte), and anti-Iba-1 antibody (microglia) by the ABC method to confirm the presence or absence of infiltration of lymphocytes in the central nerve system. The results are shown in Table 2.

TABLE 2

| | Immune tissue staining. | |
| --- | --- | --- |
| | Control group | Treatment group |
| CD4 | (−) | (−) |
| CD86 | (−) | (−) |
| CD11b | (−) | (−) |
| GFAP | (+++) | (+) |
| Iba-1 (microglia) | (+) | (++ to +++) |

The brain tissue was stained individually with the T-cell marker CD4 and the T-cell activation molecule CD86, which resulted in negative reactions in both the control group and the treatment group. It was also negative for the peripheral macrophage marker CD11b. A difference was recognized between the two groups for the astrocyte marker GFAP. An increase in the number of activated microglias (Iba-1 positive) was recognized in the frontal lobe and the temporal lobe in the treatment group.

Test 8

Tissue Staining Test 3

Tissue samples were obtained from mice received oral administration of the adeno-associated virus of Example 2 (hereinafter referred to as "treatment group 2) and the control group 6 months after the administration (at 10 months of age) and frozen sections of the tissue were used to perform DAB staining in the same manner as in Test Example 6.

Analysis of the brain 6 months after administration (at 10 months of age) revealed that amyloid deposition was clearly decreased and the number of senile plaques was drastically reduced in the treatment group 2 as compared to the control group.

Test 9

Comparison of Aβ accumulation area ratio-1

Three groups each consisting of 4 mice were set up and given oral administration of the adenovirus-associated virus of Example 1 ($5.0 \times 10^{11}$ viral genome/mouse) one time at 15 weeks of age (hereinafter referred to as "group A"), at 30 weeks of age (hereinafter referred to as "group B") or at 45 weeks of age (hereinafter referred to as "group C"), respectively. Further, the control group consisting of 6 mice was set up and given oral administration of PBS (0.1 ml/mouse) at 15 weeks of age. Then, the animals of each group were dissected at 12 to 13 months of age (52 to 56 weeks of age) to obtain brain tissue sections individually from frontal lobe cortex, temporal lobe, and hippocampus regions. These tissue sections were stained in the same manner as in Test Example 6 and observed using a 3CCD camera connected to a microscope to measure the area of Aβ accumulation in the individual regions. The ratio of Aβ accumulation area to individual measuring site was calculated. The results are shown in FIG. 4.

In the control group, the average ratio of the abovementioned Aβ accumulation area to the three measuring regions in the brain was 2.64±1.46%. On the other hand, the ratios were 0.55±0.50% in group A administered at 15 weeks of age, 0.48±0.35% in group B administered at 30 weeks of age, and 0.46±0.27% in group C administered at 45 weeks of age, respectively, and all significantly lower as compared to that in the control group (one-way variance analysis (ANOVA) and Student-t test, $p<0.001$).

Test 10

Comparison of Aβ Accumulation Area Ratio-2

Three groups each consisting of 4 mice were set up and given oral administration of the adeno-associated virus of Example 2 ($5.0 \times 10^{11}$ viral genome/mouse) one time at 15 weeks of age (hereinafter referred to as "group D"), at 30 weeks of age (hereinafter referred to as "group E") or at 45 weeks of age (hereinafter referred to as "group F"). Then, the individual groups were treated in the same manner as in Test Example 9 and the ratio of Aβ accumulation area to the individual measuring site was calculated. The results are shown in FIG. 5.

The area ratios of the abovementioned Aβ accumulation were 0.39±0.27% in group D administered at 15 weeks of age, 0.45±0.30% in group E administered at 30 weeks of age, and 0.37±0.20% in group F administered at 45 weeks of age, respectively, and all significantly lower as compared to that in the control group shown in Test Example 9 (one-way variance analysis (ANOVA) and Student-t test, $p<0.001$).

Test 11

Measurement of TGF-β1

Blood samples were taken from the mice of each group upon dissection in Test Examples 9 and 10 to obtain the serum. The concentration of TGF-β1 in the mouse serum was measured by the ELISA method using a Quantikine Mouse/Rat/Porcine TGF-β1 Immunoassay kit (R & D Systems). The results are shown in FIG. 6. The TGF-β concentration in the mouse serum was 111.6±40.0 pg/ml in the control group. On the other hand, the concentration was 80.5±12.9 pg/ml in group A, 76.0±6.3 pg/ml in group B, and 74.3±21.0 pg/ml in group C, respectively, in Test Example 9; the values in all groups were significantly lower as compared to that in the control group (one-way variance analysis (ANOVA) and Student-t test, $p<0.001$).

Further, the concentration was 99.4±21.2 pg/ml in group C, 80.2±17.2 pg/ml in group D, and 72.9±15.8 pg/ml in group E, respectively, in Test Example 10; the values in all groups were significantly lower as compared to that in the control group (one-way variance analysis (ANOVA) and Student-t test, $p<0.001$).

This application claims priority to JP 2003-169714 filed Jun. 16 30, 2003, and JP 2003-371103 filed Oct. 30, 2003. The entire contents of the above-identified applications are hereby incorporated by reference.

---

The invention claimed is:

1. A method for treating Alzheimer's disease in a mammal in need thereof, comprising orally administering to the mammal a DNA vaccine composition, wherein said composition comprises an adeno-associated virus vector encoding a β-amyloid peptide and a signal peptide capable of extracellularly secreting said β-amyloid peptide, in an operative form, wherein said administering results in suppressing formation of an amyloid plaque in the central nervous system and reducing the concentration of TGF-β1 in the blood of the mammal, and wherein administering said composition maintains therapeutic activity for at least 6 months.

2. The method according to claim 1, wherein the β-amyloid peptide is expressed in intestinal cells by the adeno-associated virus vector.

3. The method according to claim 1, wherein said β-amyloid peptide comprises the amino acids 4 to 10 of the amino acid sequence as shown in SEQ ID NO: 2.

4. The method according to claim 1, wherein the DNA encoding said β-amyloid peptide comprises the nucleotides 10 to 30 of the nucleotide sequence as shown in SEQ ID NO: 1.

5. The method according to claim 1, wherein said β-amyloid peptide comprises the amino acid sequence as shown in SEQ ID NO: 2.

6. The method according to claim 1, wherein the DNA encoding said β-amyloid peptide comprises the nucleotide sequence as shown in SEQ ID NO: 1.

7. The method according to claim 1, wherein said β-amyloid peptide comprises the amino acid sequence as shown in SEQ ID NO: 4.

8. The method according to claim 1, wherein the DNA encoding said β-amyloid peptide comprises the nucleotide sequence as shown in SEQ ID NO: 3.

9. The method according to claim 1, wherein said signal peptide is a signal peptide of amyloid precursor protein.

10. The method according to claim 1, wherein said signal peptide comprises the amino acid sequence as shown in SEQ ID NO: 6.

11. The method according to claim 1, wherein the DNA encoding said signal peptide comprises the nucleotide sequence as shown in SEQ ID NO: 5.

12. The method according to claim 1, wherein progress of cerebrovascular amyloid deposition or microvascular degeneration is suppressed.

13. The method according to claim 1, wherein anti-β amyloid peptide antibody production is induced without substantially inducing a cellular immune response.

14. The method according to claim 13, wherein the induced cellular immune response causes encephalitis.

* * * * *